(12) United States Patent
Crivello

(10) Patent No.: US 7,999,127 B2
(45) Date of Patent: Aug. 16, 2011

(54) SILOXANE MONOMERS AND OLIGOMERS

(75) Inventor: James V. Crivello, Clifton Park, NY (US)

(73) Assignee: Rensselaer Polytechnic Institute, Troy, NY (US)

( * ) Notice: Subject to any disclaimer, the term of this patent is extended or adjusted under 35 U.S.C. 154(b) by 345 days.

(21) Appl. No.: 12/397,377

(22) Filed: Mar. 4, 2009

(65) Prior Publication Data

US 2009/0176958 A1   Jul. 9, 2009

Related U.S. Application Data

(62) Division of application No. 10/559,847, filed as application No. PCT/US2004/011607 on Apr. 16, 2004, now Pat. No. 7,534,901.

(60) Provisional application No. 60/463,191, filed on Apr. 16, 2003.

(51) Int. Cl.
C07F 7/21 (2006.01)
C07F 7/08 (2006.01)
C08G 77/14 (2006.01)
C08G 77/06 (2006.01)

(52) U.S. Cl. ............. 556/460; 556/462; 528/15; 528/31

(58) Field of Classification Search .................. 556/460, 556/462; 528/15, 31
See application file for complete search history.

(56) References Cited

U.S. PATENT DOCUMENTS 5,484,950 A   1/1996 Crivello
2002/0137870 A1   9/2002 Crivello

OTHER PUBLICATIONS

Wong, C.P., "Thermal-Mechanical Enhanced High-Performance Silicone Gels and Elastomeric Encapsulants in Microelectric Packaging," IEEE Transactions on Components, Packaging, and Manufacturing Technology-Part A, vol. 18(2), pp. 270-273 (1995).
Kurian et al., "Poly(pentamethylcyclopentasiloxane). I. Synthesis and Characterization," Journal of Polymer Science: Part A: Polymer Chemistry, vol. 40, pp. 1285-1292 (2002).
Seino et al., "Catalytic Cross-Dehydrocoupling Polymerization of Phenylsilane with Water. A New Approach to Poly(phenylsilsesquioxane," Polymer Journal, vol. 35(2), pp. 197-202 (2003).
Kennedy et al., "Amphiphilic Membranes with Controlled Mesh Dimensions for Insulin Delivery," Macromol. Symp., vol. 172, pp. 56-66 (2001).
Shim et al., "Novel Thermoplastic Elastomers. III. Synthesis, Characterization, and Properties of Star-Block Copolymers of Poly(indene-b-isobutylene) Arms Emanating from Cyclosiloxane Cores," Journal of Polymer Science: Part A: Polymer Chemistry, vol. 38, pp. 279-290 (2000).
Gustavson et al., "Metal Complex-Catalyzed Redistribution Reactions of Organosilanes IV. Redistribution Reactions of Methylsiloxanes Catalyzed by Transition Metal Complexes," Journal of Organometallic Chemistry, vol. 238, pp. 87-91 (1987).
Suzuki et al., "New aspects of platinum-catalyzed hydrosilylation of disilylethynes," Journal of Organometallic Chemistry, vol. 396, pp. 299-305 (1990).
Crivello et al., "The Synthesis, Characterization, and Photoinitiated Cationic Polymerization of Silicon-Containing Epoxy Resins," Journal of Polymer Science: Part A: Polymer Chemistry, vol. 28, pp. 479-503 (1990).
Crivello et al., "New Epoxy Functional Silicone Monomers for Cationic UV Curing," Radach Conference Proceedings, pp. 432-445 (1990).
Crivello et al., "UV Cure of Epoxy-Silicone Monomers," Am. Chem. Society, Chapter 28, pp. 398-411 (1990).
Crivello et al., "The UV Cure of Epoxy-Silicone Monomers," PMSE, vol. 60, pp. 217-227 (1989).
International Search Report from International Application No. PCT/US2004/011607 completed Feb. 14, 2005 and mailed on Mar. 4, 2005.

*Primary Examiner* — Bernard Dentz
(74) *Attorney, Agent, or Firm* — Heslin Rothenberg Farley & Mesiti P.C.

(57) ABSTRACT

A process for preparing a cationically photopolymerizable siloxane oligomer, that includes: combining a platinum group catalyst, a hydrosiloxane compound selected from

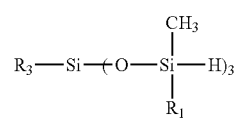

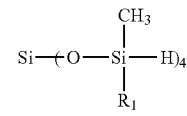

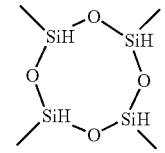

and a vinyl or allyl compound comprising a cationically photopolymerizable functionality; and then contacting the product with oxygen in the presence of the catalyst to form the cationically photopolymerizable multifunctional siloxane oligomer. $R_1$ and $R_3$ are independently fluoroethyl, methyl or phenyl.

9 Claims, No Drawings

SILOXANE MONOMERS AND OLIGOMERS

CROSS-REFERENCE TO RELATED APPLICATIONS

This application is a divisional of U.S. patent application Ser. No. 10/559,847, filed on Dec. 7, 2005 (filing requirements completed on Apr. 27, 2006), which is a 35 U.S.C. §371 U.S. national stage filing from PCT Application Ser. No. PCT/US04/11607 having international filing date of Apr. 16, 2004, published in English under WO 2004/094435 A2 on Nov. 4, 2004, which claims priority from U.S. Provisional Application Ser. No. 60/463,191, filed Apr. 16, 2003; the entire disclosure of the aforementioned are incorporated herein by reference.

BACKGROUND OF THE INVENTION

Interest and research activity in the photoinitiated cationic crosslinking polymerizations of multifunctional epoxide and oxetanes monomers have increased rapidly as this technology has found broad use in many industrial applications. Decorative and protective coatings, printing inks and adhesives are just a few examples of those applications in which photoinitiated cationic polymerizations have experienced the most commercial growth. There are several major motivating factors driving the adoption of this technology. First, the ability to conduct these crosslinking polymerizations very rapidly, with low energy and without the use of an inert atmosphere provides important economic incentives. Second, since solvents are not employed, there are no emissions and consequently, the environmental consequences of these polymerizations are minimal. Lastly, the thermal, mechanical, chemical resistance, low shrinkage and adhesion characteristics of the network polymers that are formed are excellent. The industrial impact of photoinitiated polymerizations in general and photoinitiated cationic polymerizations in particular, is predicted to increase markedly in the future as this technology undergoes further maturation.

Early work in the field of cationic photopolymerization took advantage of commercially available epoxide monomers. These epoxide monomers were and still are widely employed in thermally induced condensation polymerizations together with coreactants such as amines, anhydrides and thiols for such purposes as coatings, adhesives, potting and encapsulating resins. They were not intended for use in cationic ring-opening addition polymerizations. Consequently, such monomers are not optimally designed for nor in many cases do they possess sufficient purity for this purpose. As the uses of photoinitiated cationic polymerizations in advanced applications increase, in many cases, these epoxides no longer meet the required higher performance characteristics that are demanded. For these reasons, there has been a long-standing interest in this laboratory in the design and synthesis of novel epoxide monomers expressly for use in cationic photopolymerizations.

The synthesis of epoxy-functional siloxanes has been described in several publications (Crivello, J. V.; Lee, J. L. *Polym. Mtls. Sci. and Eng. Preprints,* 1989, 60, 217; *ACS Symposium Series No.* 417, C. E. Hoyle and J. F. Kinstle, editors 1989, p. 398; Crivello, J. V.; Lee, J. L. *J. Polym. Sci., Polym. Chem. Ed.,* 1990, 28, 479; Crivello, J. V.; Lee, J. L. *Proc. of the RADTECH '90 North America Conf.,* Chicago, Mar. 25, 1990, p. 432). The structures of two typical examples of this class of monomers, I and II, are shown below.

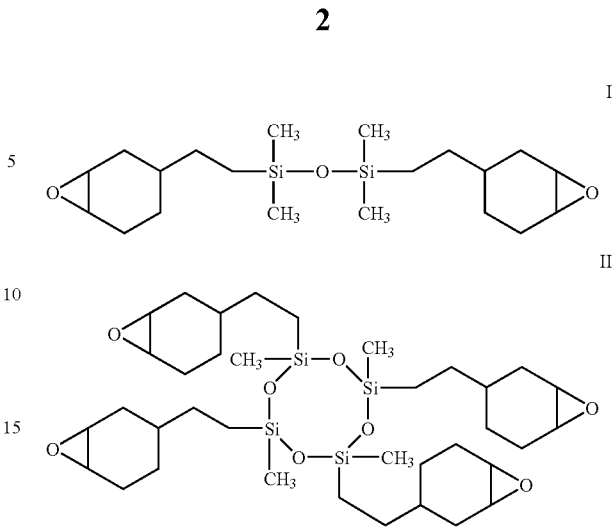

These di- and tetrafunctional monomers, respectively, bearing epoxycyclohexane groups display high rates of photoinitiated cationic polymerization. For example, the photoinitiated cationic ring-opening polymerization of I is faster by a factor of at least ten when compared to the commercially available 3,4-epoxycyclohexylmethyl 3',4'-epoxycyclohexanecarboxylate. This latter compound is considered a "high reactivity epoxide" and is currently employed in most cationic photopolymerizations where epoxide monomers are used.

However, while monomers such as I and II undergo efficient cationic ring-opening photopolymerization to give crosslinked materials with excellent thermal and chemical resistance, they produce hard, brittle, glass-like materials with little elongation and flexibility. Therefore, there remains a need for additional epoxy silicone monomers with different backbone structures, in order to expand the range of mechanical properties obtainable from this class of monomers.

It has been reported that the hydrosilation of α, ω-Si—H difunctional polydimethylsiloxanes containing up to four silicon atoms with vinyl compounds can be carried out under conditions that give essentially quantitative yields of the monosubstituted products. (See, for example, US 2002-0137870-A1.) This reaction is quite unique and has no parallel in carbon chemistry. For example, the condensation of TMDS with VCHO takes place in toluene or 1,4-dioxane at 65° C. in the presence of Wilkinson's catalyst (tristriphenylphosphinerhodium(I) chloride) to give 98% of the desired monoaddition product. In contrast, at higher temperatures, the reaction is indiscriminate and a mixture of IV, II and unreacted TMDS are obtained.

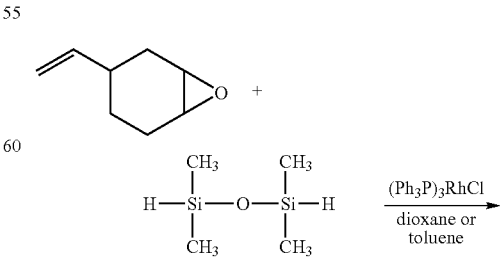

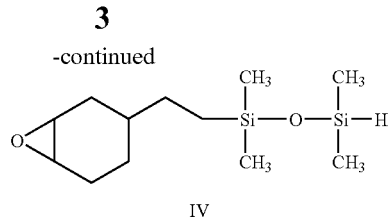

IV

Similarly, monohydrosilated products are also obtained using 1,1,3,3,5,5-hexamethyltrisiloxane and 1,1,3,3,5,5,7,7-octamethyltetrasiloxane in greater than 94% yields.

A wide variety of highly reactive di- and multifunctional epoxy silicone monomers can be synthesized by the straightforward use of the hydrosilation reaction. For example, I can be prepared directly in virtually quantitative yield by the reaction shown in involving the addition of a 2:1 stoichiometric ratio of 4-vinyl-1-cyclohexene-1,2-epoxide (VCHO) to 1,1,3,3-tetramethyldisiloxane (TMDS) typically at a temperature above 100° C. in the presence of a platinum or rhodium catalyst.

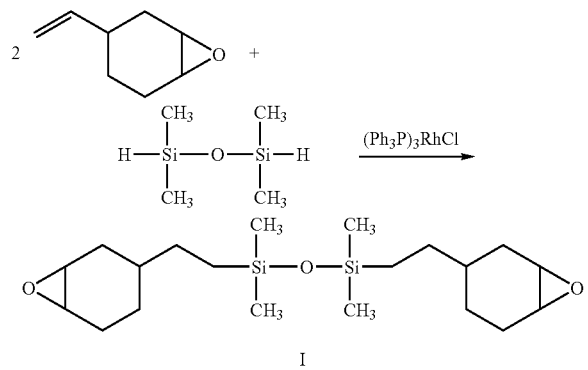

I

The same reaction can be carried out with other α, ω-Si—H difunctional polydimethylsiloxanes to extend the length of the siloxane chain between the reactive epoxycyclohexane groups. In addition, a wide assortment of other epoxy functional vinyl compounds can also be employed in this hydrosilation reaction. However, obtaining the α, ω-Si—H difunctional polydimethylsiloxanes of higher molecular weight, that is, with chains containing more than two silicon atoms, with specific, well-defined chain lengths is both problematic and expensive. Typically, such materials are obtained as mixtures containing a broad distribution of chain lengths from the cohydrolysis of dimethyldichlorosilane and dimethylchlorosilane. The mixture is then fractionally distilled to isolate the species with the desired chain length. As the chain length of these materials increases, it becomes increasingly difficult to separate the different species present due to the similarity of their boiling points. For this reason, α, ω-Si—H difunctional oligomeric olydimethylsiloxanes containing more than two silicon atoms are generally prepared only in small laboratory quantities.

Several reports have appeared in the literature, describing the conversion of Si—H bonds to siloxane groups by a dehydrodimerization reaction. Kennedy, et al. have described the condensation of Si—H containing cyclic siloxanes in the presence of water and a platinum catalyst to prepare amphiphilic networks composed of siloxanes and polyolefins (Kennedy, et al., *Macromol. Symp.* 172, 56-66 (2002). Kawakami et al have carried out the condensation of phenylsilane with water in the presence of platinum and other noble metal catalysts to obtain branched oligomeric resins (Seino, et al., *Polymer Journal,* 35, 197-202 (2003). In both cases, a complex mixture of siloxane products was obtained.

SUMMARY OF THE INVENTION

It has been unexpectedly found that it is possible to carry out the efficient dehydrodimerization of a monohydrosiloxane compound to give a well-characterized, α, ω-functional siloxane dimer of high purity by heating in the presence of oxygen and a platinum group catalyst.

Accordingly, in one aspect, the present invention relates to a process for preparing an α, ω-functional siloxane compound in a purity of greater than or equal to 90%. The process includes contacting a monohydrosiloxane compound of formula 1

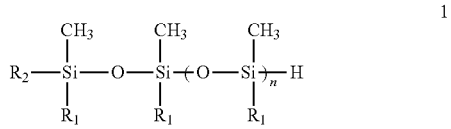

1 with oxygen in the presence of a platinum group catalyst, without adding water, to form the α, ω-functional siloxane compound in a purity of greater than or equal to 90%; wherein n is 0, 1, or 2; $R_1$ is fluoroethyl, methyl or phenyl; and $R_2$ is substituted alkyl, epoxyalkyl, oxetanylalkyl, substituted oxaalkyl, epoxyoxaalkyl, oxetanyloxaalkyl, alkenyl, alkylalkoxysilyl, substituted alkylaryl, and substituted arylalkyl.

In another aspect, the invention relates to a process for preparing a cationically photopolymerizable siloxane oligomer. The process includes combining a platinum group catalyst, a hydrosiloxane compound selected from

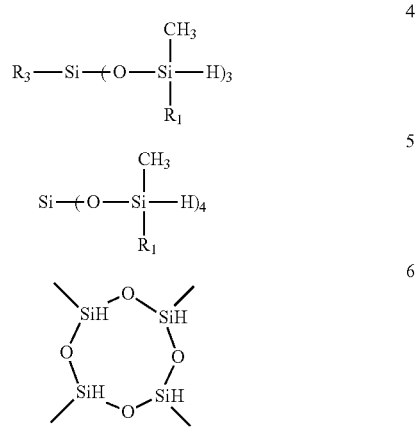

and a vinyl or allyl compound comprising cationically photopolymerizable functionality; and contacting the product with oxygen in the presence of the catalyst to form the cationically photopolymerizable multifunctional siloxane oligomer, wherein $R_1$ is fluoroethyl, methyl or phenyl and $R_3$ is methyl or phenyl.

DETAILED DESCRIPTION OF THE INVENTION

The present invention relates to a process for preparing an α, ω-functional siloxane compound in a purity of greater than or equal to 90% by contacting a monohydrosiloxane compound of formula 1

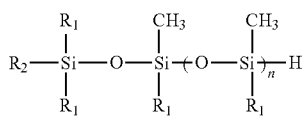

with oxygen in the presence of a platinum group catalyst, without adding water, to form the α, ω-functional siloxane compound in a purity of greater than or equal to 90%. In formula 1, n is 0, 1, or 2; $R_1$ is fluoroethyl, methyl or phenyl; and $R_2$ is substituted alkyl, epoxyalkyl, oxetanylalkyl, substituted oxaalkyl, epoxyoxaalkyl, oxetanyloxaalkyl, alkenyl, alkylalkoxysilyl, substituted alkylaryl, or substituted arylalkyl. In the context of the present invention, the term 'substituted' refers to substitution with functional group(s) such as haloalkyl, alkoxy, carbonyl, carboxy, carboxalkoxy, carboxamido, acyloxy, amidino, nitro, halogen, hydroxy, OCH$(COOH)_2$, cyano, primary amino, secondary amino, acylamino, alkylthio, sulfoxide, sulfone, phenyl, benzyl, phenoxy, benzyloxy, heteroaryl, or heteroaryloxy. The process is illustrated in Scheme 1.

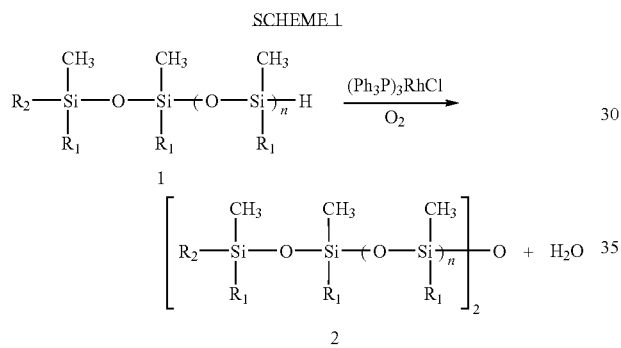

For 1 and 2, $R_1$ is preferably methyl.

In the context of the present invention, the term 'α, ω-siloxane' refers to a siloxane compound of formula 2 containing 4-8 silicon atoms, wherein both terminal silicon atoms are substituted with substituted alkyl, epoxyalkyl, oxetanylalkyl, substituted oxaalkyl, epoxyoxaalkyl, oxetanyloxaalkyl, alkenyl, alkylalkoxysilyl, substituted alkylaryl, or substituted arylalkyl groups. Essentially any group that is attachable to a vinyl or allyl group and that is not oxidized under conditions of the reactions may be used as $R_2$. In preferred embodiments, $R_2$ contains a reactive group, more preferably, a polymerizable group such as a vinyl ether, 1-propenyl ether, acrylate, methacrylate, epoxy, oxetanyl, or alkoxysilyl group, and most preferably, epoxy group.

The α, ω-siloxane is formed by contacting, combining or mixing a monohydrosiloxane with oxygen in the presence of a platinum group catalyst, without adding water. Platinum group catalyst' means a metal compound or complex that contains platinum, palladium or rhodium. A preferred catalyst is a rhodium compound, particularly Wilkinson's catalyst, $(Ph_3P)_3RhCl$, especially polymer-bound Wilkinson's catalyst (PBWC). PBWC is particularly advantageous since it can be easily removed from the reaction mixture during workup by a simple filtration.

The dehydrodimerization reaction may be carried out efficiently by heating the monohydrosiloxane compound in the presence of oxygen and the catalyst, over a period of time that typically ranges from about four to about six hours. The length of heating period is not critical and may be determined on an individual case basis. For the sake of simplicity, only Wilkinson's catalyst is shown in the above and in later equations. The reaction can be readily monitored during the reaction by following the disappearance of the Si—H singlet peak at 4.6-4.7 ppm in the $^1$H-NMR.

Suitable solvents for the coupling reaction are compatible with all of the reagents. Examples include aromatic solvents such as toluene, as well as cyclohexane, THF, glyme diglyme and 1,4-dioxane. However, it is noted that the overall reaction proceeds more rapidly in glyme, diglyme and 1,4-dioxane than in toluene.

The reaction involves the rhodium-catalyzed oxidation of the Si—H bond by molecular oxygen. Previous work (Kennedy and Seino, above) had indicated that the platinum catalyzed dehydrodimerization reaction requires water. Several experiments confirmed that, in this specific case, oxygen and not water is involved. When the dehydrodimerization of IV was attempted by bubbling wet nitrogen gas through the reaction mixture, no coupling took place. However, when dry air was passed into the reaction mixture, rapid coupling to afford V took place. Direct oxidative coupling of two Si—H groups to form the siloxane may take place. While applicant does not wish to be held to any particular mechanistic theory, it is more probable that the coupling process takes place by a stepwise sequence of reactions as shown in Scheme 2 involving first, the oxidation of a Si—H group by oxygen to produce a silanol (SiOH) moiety. Thereafter, rapid condensation of the silanol with unreacted Si—H groups with the elimination of hydrogen would lead to the production of the coupled siloxane product. This latter reaction has considerable precedent in the literature.

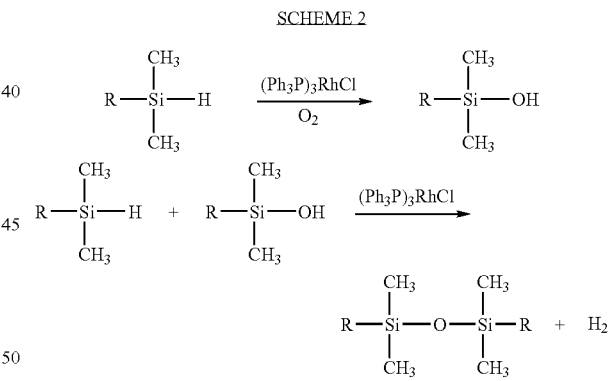

Although it is acknowledged that water is generated by the coupling reaction, added water appears to lead to the production of unwanted side products. Therefore, the dehydrodimerization process of the present invention includes only water produced by the reaction. A particular advantage of the process of the present invention is that where pure starting materials are used, pure products are obtained. Specifically, where the monohydrosiloxane compound has a purity of ≦90%, preferably ≦95%, and more preferably, ≦99%. In contrast, prior art processes utilizing additional water yielded complex mixtures of products.

The $R_2$ group in formula 1 may be derived from a vinyl or allyl compound, or is derivable therefrom, particularly one of the following, by addition of the vinyl or allyl compound to a monohydrosilane compound:

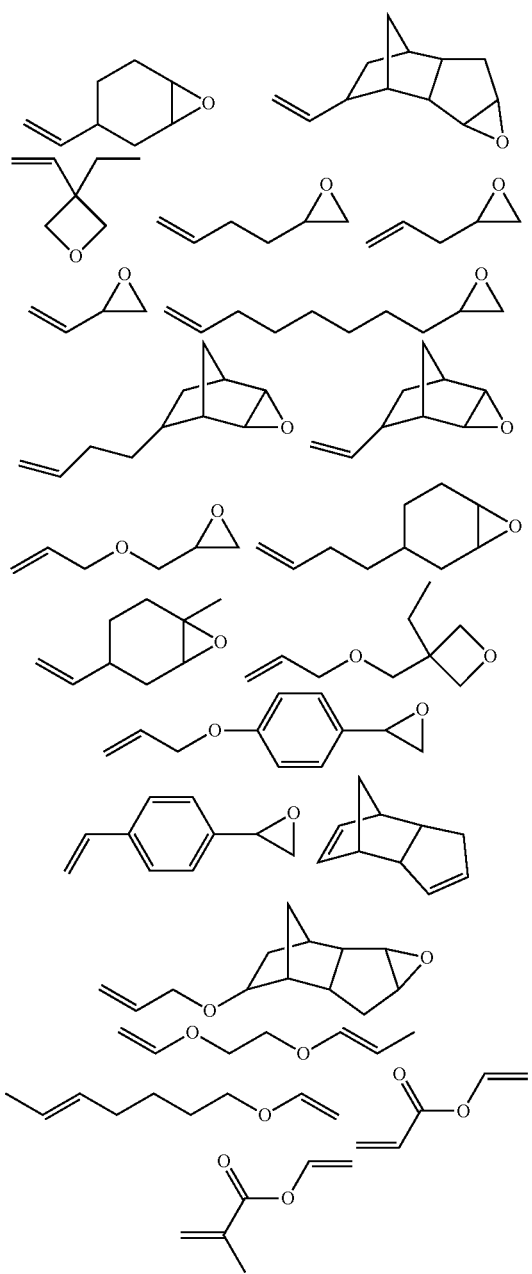

Preferably, R₂ is derived from one or more of the following:

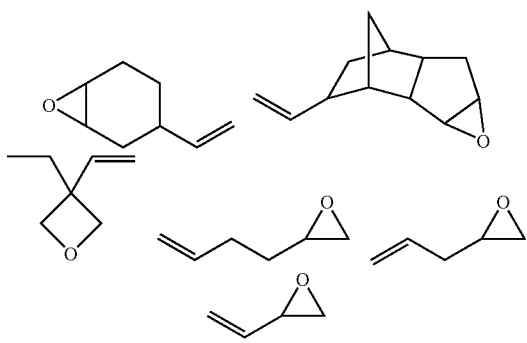

α, ω-Siloxanes wherein R₂ is derived from 4-vinylcyclohexane oxide (VCHO) are particularly preferred, as they are highly reactive toward cationic photopolymerization.

R₂ may be derived from a vinyl or allyl compound in a step preceding dehydrodimerization reaction shown in Scheme 1, where the monohydrosiloxane compound 1 is formed by combining the platinum group catalyst, a vinyl or allyl precursor for R₂ and a dihydrosiloxane compound of formula 3, having a purity of greater than or equal to 90%,

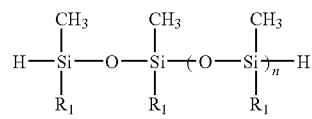

wherein $R_1$ is again fluoroethyl, methyl or phenyl. This reaction is illustrated in Scheme 3.

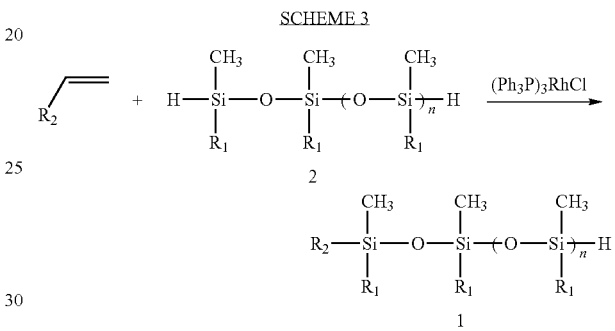

In general, the dihydrosiloxane compound and the vinyl or allyl compound are present in a 1:1 ratio on a molar basis, that is, one mole of vinyl or allyl compound per mole of the dihydrosiloxane compound. (Each molar equivalent dihydrosiloxane compound contains two labile or reactive hydrogen atoms.)

In a variation of the process, the vinyl compound may be a compound containing more than one double bond, as, for example, the dicyclopentadiene compound 4, which yields a monohydrosiloxane having a terminal double bond. This reaction is shown below in Scheme 4.

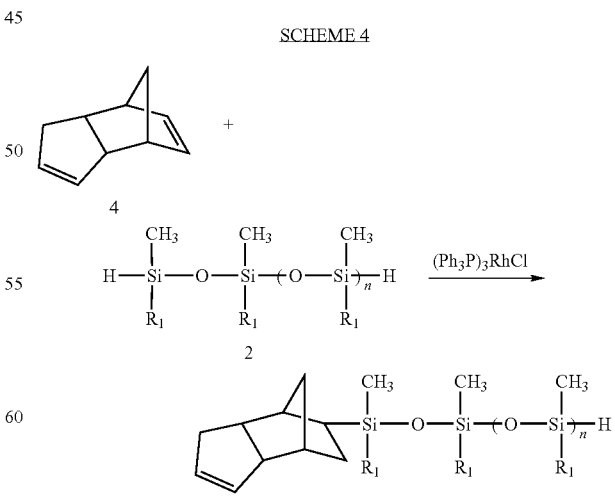

Many reactions for converting a double bond to another functional group are known in the art. In particular, the α, ω-functional siloxane may be epoxidized to form an epoxydicyclopentadiene group. The double bond may be converted at the stage shown in Scheme 3, or after the dehydrodimerization.

In another embodiment, the present invention relates to a process for preparing a cationically photopolymerizable siloxane oligomer, illustrated in Schemes 5 and 6.

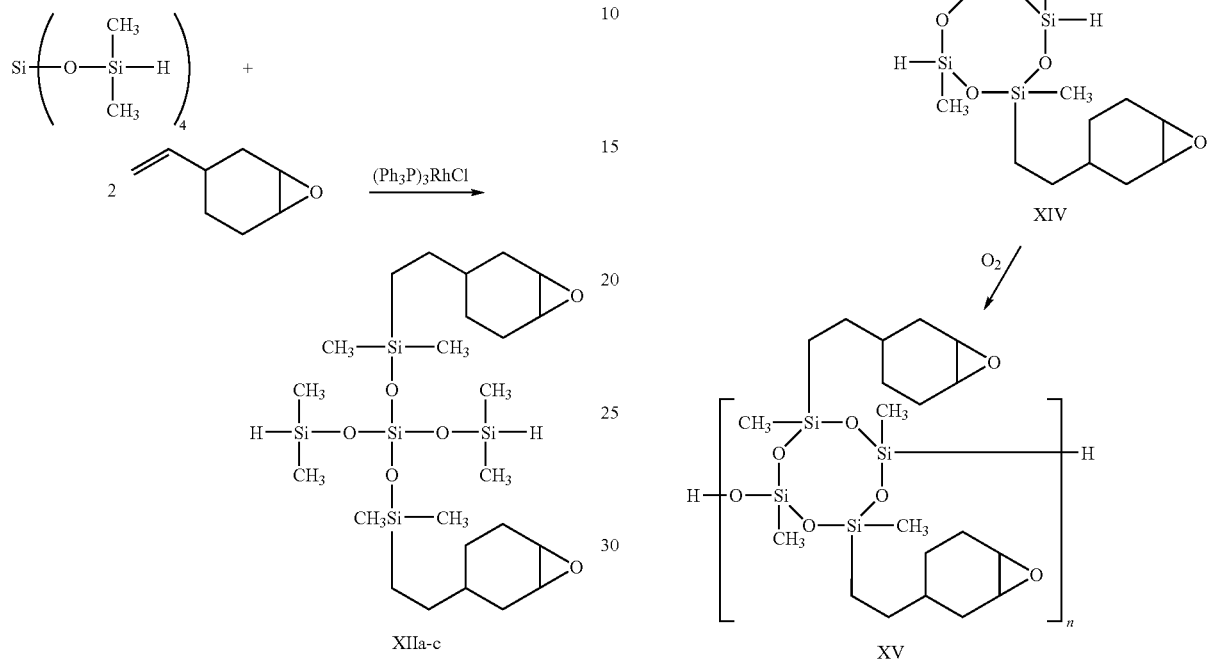

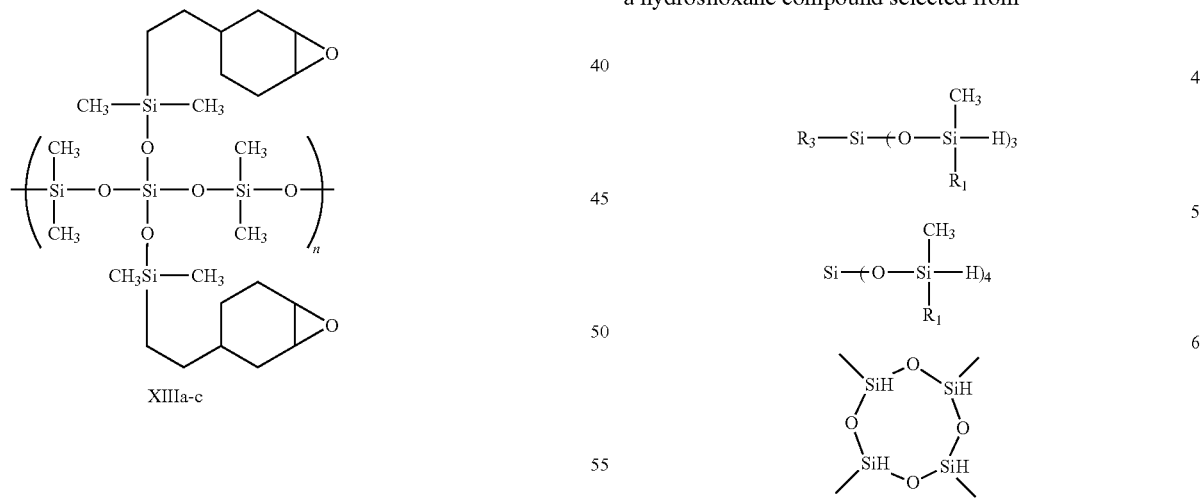

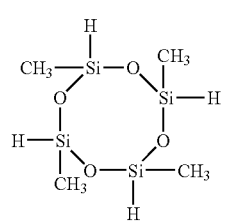

The process includes combining a platinum group catalyst, a hydrosiloxane compound selected from and a vinyl or allyl compound comprising cationically photopolymerizable functionality; and contacting the product with oxygen in the presence of the catalyst to form the cationically photopolymerizable multifunctional siloxane oligomer. The process wherein hydrosiloxane 4 is utilized is not shown. In the structures, $R_1$ is fluoroethyl, methyl or phenyl and $R_3$ is methyl or phenyl. The vinyl or allyl compound is preferably one of those shown above, especially, 4-vinylcyclohexaneoxide. The catalyst for the reaction is the same as above, especially $(Ph_3P)_3RhCl$.

By combining the hydrosilation and dehydrodimerization reactions, the synthesis of V can be carried out as a streamlined two-step, one-pot reaction in high yield directly from TMDS and VCHO without the need for the isolation of the intermediate, IV. In a similar fashion, the preparation of a number of additional α, ω-difunctional compounds were carried out using a variety of vinyl substituted compounds and α, ω-SiH difunctional siloxanes as starting materials. All of the compounds prepared were high boiling colorless liquids. Isolation and purification of the coupled compounds consisted of passing the reaction mixtures through a short column of silica gel using cyclohexene as an eluent followed by removal of the solvent under reduced pressure. This process served to remove the rhodium catalyst and to decolorize the product. Each compound was characterized by means of its $^1$H-NMR and elemental analysis. Comparison of the $^1$H-NMR spectrum of monomer V prepared by the streamlined, one-pot, two-step procedure, with that of a sample of V prepared by direct double hydrosilation of 1,1,3,3,5,5,7,7-octamethyltetrasiloxane with two equivalents of VCHO showed that the two compounds were identical. As expected, the $^{29}$Si—NMR spectrum of V showed two resonances corresponding to the two different types of silicon atoms in the molecule. Analogues of V containing six silicon atoms (VI) and bearing linear open chain epoxide groups (VII, VIII and IX), oxetanes (X) and trimethoxysilyl groups (XI) were also prepared. It appears from these studies that the rhodium catalyzed dehydrodimerization reaction is a versatile and broadly applicable synthetic method that is compatible with a number of different types of polymerizable functional groups.

The α, ω-functional siloxane monomers or oligomers may be polymerized by various means. For example, the epoxy functional oligomers may be combined with amine or anhydride curing agents and polymerized by traditional thermal methods. Acrylate and methacrylate functional oligomers may be similarly thermally cured through the use of conventional peroxide, azo, or metal-containing free radical initiators. Alternatively, these resins may be also free radical photopolymerized employing, for example, benzoin alkyl ethers, acylphosphine oxides, 1,1-diethoxyacetopheone, 1-benzoylcyclohexanol and the like as photoinitiators. Epoxy, 1-propenyl ether, 1-butenyl ether, oxetane and vinyl ether functional oligomers can be photopolymerized using UV or visible light irradiation in the presence of diaryliodonium, dialkylphenacylsulfonium, triarylsulfonium salt, and ferrocenium salt photoinitiators. The aforementioned resin-photoinitiator mixtures may be also effectively cured in the presence of the above onium salts using e-beam or $^{60}$Co gamma ray irradiation.

Materials produced by the process of the invention have many applications. Such coupling agents are widely used in the composites and reinforced plastic industries. The polymerizable siloxane monomers and oligomers may be employed as protective and abrasion resistant coatings for wood metals, plastics and glass. They may be employed as adhesive or bonding agents. Combined with fibrous reinforcing agents they may be cured by UV and e-beam radiation to give high performance composites. They may be further used as curable encapsulating and potting agents for electronic and microelectronic applications. Further uses lie in resins for stereolithography, holographic recording and as optical adhesives, fiber optic coatings and wave guides in photonic applications. In the course of their use in various applications, the resins may be combined with various fibrous or particulate reinforcing agents, flow control and flatting agents, photosensitizers, pigments and dyes and mold releases.

The use of the combination of the rhodium-catalyzed hydrosilation followed by a dehydrodimerization reaction provides a simple, direct and high yield route to the synthesis of well-characterized epoxy- and oxetane-functional siloxane monomers and oligomers. Studies of the cationic photopolymerizations of the monomers prepared in this study showed that those monomers containing epoxycyclohexyl groups were considerably more reactive than comparable monomers bearing-open chain epoxy groups. Both of these latter types of monomers were more reactive than commercially available biscycloaliphatic epoxy monomers. Comparing analogous difunctional epoxy siloxane monomers with different siloxane chain lengths, it was observed that the lengths of the chains did not greatly affect their reactivity in cationic photopolymerization. The slight decrease in the rate with increasing siloxane chain length can be ascribed to a decrease in the functional group density. Oligomers bearing pendant epoxycyclohexyl groups also displayed excellent reactivity in photoinitiated cationic polymerization. This new synthetic route for the preparation of epoxy functional siloxanes offers the possibility of greatly increasing the availability of these monomers and also extending the range of their mechanical properties. Recently, it has been announced that epoxycyclohexyl-functional siloxanes are the materials of choice for holographic data storage media. The materials described here should find use in this as well as other applications.

It should be noted that any numerical values recited herein include all values from the lower value to the upper value in increments of one unit provided that there is a separation of at least 2 units between any lower value and any higher value. As an example, if it is stated that the number of carbon or oxygen atoms, the amount of a coreactant, a value of a process variable such as temperature, pressure, or time, ranges, for example, from 1 to 90, preferably from 20 to 80, more preferably from 30 to 70, it is intended that values such as 15 to 85, 22 to 68, 43 to 51, 30 to 32 etc. are expressly enumerated in this specification. For values which are less than one, one unit is considered to be 0.0001, 0.001, 0.01 or 0.1 as appropriate. These are only examples of what is specifically intended and all possible combinations of numerical values between the lowest value and the highest value enumerated are to be considered to be expressly stated in this application in a similar manner.

In the context of the present invention, alkyl is intended to include linear, branched, or cyclic hydrocarbon structures and combinations thereof. Lower alkyl refers to alkyl groups of from 1 to 4 carbon atoms. Lower alkyl groups include methyl, ethyl, n-propyl, isopropyl, and n-, s- and t-butyl. Preferred alkyl groups are those of $C_{20}$ or below. Cycloalkyl is a subset of alkyl and includes cyclic hydrocarbon groups of from 3 to 8 carbon atoms. Examples of cycloalkyl groups include cyclopropyl, cyclobutyl, cyclopentyl, and norbornyl.

Aryl and heteroaryl mean a 5- or 6-membered aromatic or heteroaromatic ring containing 0-3 heteroatoms selected from nitrogen, oxygen or sulfur; a bicyclic 9- or 10-membered aromatic or heteroaromatic ring system containing 0-3 heteroatoms selected from nitrogen, oxygen or sulfur; or a tricyclic 13- or 14-membered aromatic or heteroaromatic ring system containing 0-3 heteroatoms selected from nitrogen, oxygen or sulfur. The aromatic 6- to 14-membered carbocyclic rings include, for example, benzene, naphthalene, indane, tetralin, and fluorene; and the 5- to 10-membered aromatic heterocyclic rings include, e.g. imidazole, pyridine, indole, thiophene, benzopyranone, thiazole, furan, benzimidazole, quinoline, isoquinoline, quinoxaline, pyrimidine, pyrazine, tetrazole and pyrazole.

Arylalkyl means an alkyl residue attached to an aryl ring. Examples are benzyl and phenethyl. Heteroalkylaryl means an alkyl residue attached to a heteroaryl ring. Examples include pyridinylmethyl and pyrimidinylethyl. Alkylaryl means an aryl residue having one or more alkyl groups attached thereto. Examples are tolyl and mesityl.

Alkoxy or alkoxyl refers to groups of from 1 to 8 carbon atoms of a straight, branched, cyclic configuration and combinations thereof attached to the parent structure through an oxygen. Examples include methoxy, ethoxy, propoxy, isopropoxy, cyclopropyloxy, and cyclohexyloxy. Lower alkoxy refers to groups containing one to four carbons.

Acyl refers to groups of from 1 to 8 carbon atoms of a straight, branched, cyclic configuration, saturated, unsaturated and aromatic and combinations thereof, attached to the parent structure through a carbonyl functionality. One or more carbons in the acyl residue may be replaced by nitrogen, oxygen or sulfur as long as the point of attachment to the parent remains at the carbonyl. Examples include acetyl, benzoyl, propionyl, isobutyryl, t-butoxycarbonyl, and benzyloxycarbonyl. Lower-acyl refers to groups containing one to four carbons.

Heterocycle means a cycloalkyl or aryl residue in which one to two of the carbons is replaced by a heteroatom such as oxygen, nitrogen or sulfur. Examples of heterocycles that fall within the scope of the invention include pyrrolidine, pyrazole, pyrrole, indole, quinoline, isoquinoline, tetrahydroisoquinoline, benzofuran, benzodioxan, benzodioxole (commonly referred to as methylenedioxyphenyl, when occurring as a substituent), tetrazole, morpholine, thiazole, pyridine, pyridazine, pyrimidine, thiophene, furan, oxazole, oxazoline, isoxazole, dioxane, and tetrahydrofuran.

Substituted refers to residues, including, but not limited to, alkyl, alkylaryl, aryl, arylalkyl, and heteroaryl, wherein up to three H atoms of the residue are replaced with substituted alkyl, substituted alkynyl, haloalkyl, alkoxy, carbonyl, carboxy, carboxalkoxy, carboxamido, acyloxy, amidino, nitro, halogen, hydroxy, OCH(COOH)$_2$, cyano, primary amino, secondary amino, acylamino, alkylthio, sulfoxide, sulfone, phenyl, benzyl, phenoxy, benzyloxy, heteroaryl, or heteroaryloxy. Epoxyalkyl includes the following compounds:

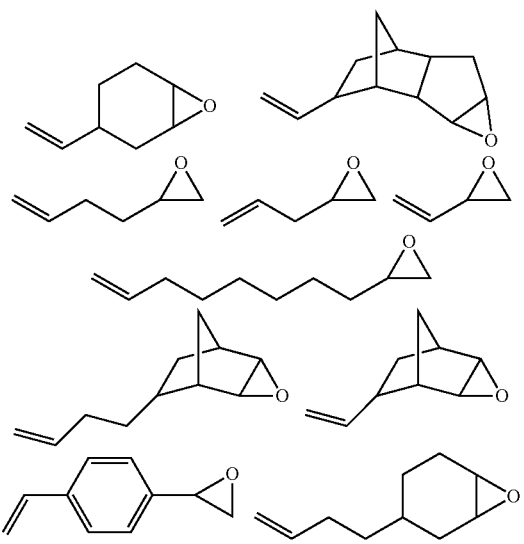

Epoxyoxaalkyl includes the following compounds:

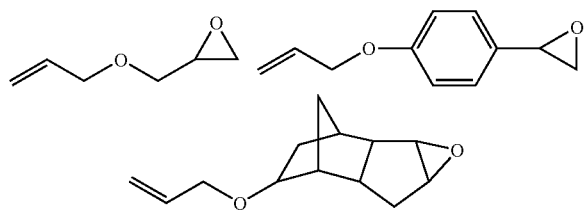

Oxetanylalkyl includes

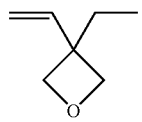

and oxetanyloxaalkyl includes

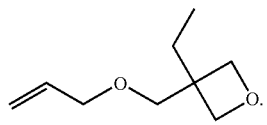

Alkenyl includes

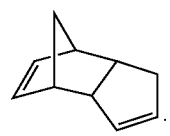

Haloalkyl refers to an alkyl residue, wherein one or more H atoms are replaced by halogen atoms; the term haloalkyl includes perhaloalkyl. Examples of haloalkyl groups that fall within the scope of the invention include CH$_2$F, CHF$_2$, and CF$_3$.

Oxaalkyl refers to an alkyl residue in which one or more carbons have been replaced by oxygen and attached to the parent structure through an oxygen. Examples include methoxypropoxy, 3,6,9-trioxadecyl and the like. The term oxaalkyl is intended as it is understood in the art [see *Naming and Indexing of Chemical Substances for Chemical Abstracts*, published by the American Chemical Society, ¶ 196, but without the restriction of ¶ 127(a)], i.e. it refers to compounds in which the oxygen is bonded via a single bond to its adjacent atoms (forming ether bonds); it does not refer to doubly bonded oxygen, as would be found in carbonyl groups. Similarly, thiaalkyl and azaalkyl refer to alkyl residues in which one or more carbons has been replaced by sulfur or nitrogen, respectively. Examples include ethylaminoethyl and methylthiopropyl.

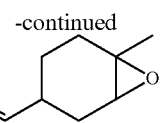

EXAMPLES

Materials

All organic starting materials and reagents employed in this investigation were reagent quality and were used as purchased unless otherwise noted. All silanes and siloxanes were purchased from Gelest, Inc. (Tullytown, Pa.). 3-Vinyl-7-oxabicyclo[4.1.0]heptane (4-vinyl-1,2-epoxycyclohexane, VCHO) was obtained from the Union Carbide Corp. (Bound Brook, N.J.). 3-Allyloxymethyl-3-ethyloxetane was a gift of the Toagosei Chemical Co. (Nagoya, Japan). Tri(triphenylphosphine)rhodium(I) chloride (Wilkinson's catalyst) and polymer-bound Wilkinson's catalyst were purchased from Strem Chemicals, (Newburyport, Mass.). The photoinitiators, (4-n-decyloxyphenyl)phenyliodonium hexafluoroantimonate, (4-n-decyloxyphenyl) diphenylsulfonium hexafluoroantimonate and S-n-dodecyl-S-methyl-S-phenacylsulfonium hexafluoroantimonate were prepared as described in earlier publications from this laboratory. Elemental analyses were performed by Atlantic Microanalysis (Norcross, Ga.).

Example 1

Synthesis of (1,7-Bis(1,2-epoxycyclohexyl-4-ethyl))-1,1,3,3,5,5,7,7-octamethyl-tetrasiloxane (V) by HydrosilatioN To a 100 mL round-bottom flask fitted with a magnetic stirrer and a reflux condenser were added 8.48 g (0.03 mol) of 1,1,3,3,5,5,7,7-octamethytetrasiloxane, 8.70 g (0.075 mol) of 3-vinyl-7-oxabicyclo[4.1.0]heptane, 40 mL of freshly distilled dry toluene. There were added 11 mg of polymer-bound Wilkinson's catalyst and the reaction mixture heated at 100-115° C. for 48 h by means of an oil bath. The course of the reaction was monitored using infrared spectroscopy by following the disappearance of the Si—H band at 2125 cm$^{-1}$. When the infrared band had completely disappeared, the reaction was terminated and the reaction mixture filtered to remove the catalyst. The unreacted starting materials and solvent were removed under reduced pressure and high vacuum.

After purification by flash chromatography over silica gel using chloroform as an eluent, there were obtained 15.3 g (96% theory) of the desired product as a colorless oil. $^1$H NMR (CDCl$_3$, 500 MHz) δ (ppm) 3.12 (m, 4H, O—CH-epoxy ring), 2.18-0.77 (m, 18H, —CH$_2$-cyclohexane ring), 0.48 (m, 4H, —CH$_2$—Si), 0.04 (s, 24H, CH$_3$—Si).

Preparation of α ω-Difunctional Monomers Using Coupled Oxidation and Dehydrodimerization. The preparation of the series of α ω-difunctional monomers with structures shown in Table 1 were carried out in a similar manner. Two typical examples of the synthetic methodology are presented below.

Example 2

Synthesis of (1,7-Bis(1,2-epoxycyclohexyl-4-ethyl))-1,1,3,3,5,5,7,7-octamethyl-tetrasiloxane (V) by Dehydrodimerization Into a 100 mL round-bottom flask fitted with a magnetic stirrer and a reflux condenser were added 6.72 g (0.05 mol) of 1,1,3,3-tetramethyldisiloxane (TMDS), 6.83 g (0.055 mol) of 3-vinyl-7-oxabicyclo[4.1.0]heptane, 15 mL of freshly distilled toluene or 1,4-dioxane and approximately 7 mg of polymer-bound Wilkinson's catalyst. The reaction mixture was heated at 65-70° C. for 10 h. The progress of the reaction was followed by $^1$H NMR in CDCl$_3$ by monitoring the reduction in the intensity of the Si—H band (4.67 ppm) due to the starting material, TMDS and the loss of the olefinic protons (4.93 and 5.7 ppm) of the vinyl epoxide. After 5 h reaction, 99% of the starting epoxide was consumed (step 1).

After cooling to room temperature, there were added 3-4 drops of triethylamine as an inhibitor and the reaction vessel fitted with an air inlet and a water trap. The flask was heated at 90-95° C. for 12 h while air was slowly bubbled through the reaction mixture. Then, the reaction mixture was cooled to room temperature and subjected to flash chromatography over silica gel using cyclohexane as the eluent. The resulting solution was dried over anhydrous sodium sulfate, filtered and the solvent and excess starting materials were removed first using a rotary evaporator. A colorless to very pale yellow oil was obtained and further dried for one day under high vacuum. There were obtained 12.3 g (92% theory) of product which gave the same $^1$H NMR spectrum as an authentic sample of 1,1,3,3,5,5,7,7-octamethyl-1,3-bis(2-(4-epoxycyclohexylethyl)tetrasiloxane prepared by direct double hydrosilation of 1,1,3,3,5,5,7,7-octamethyltetrasiloxane with 3 vinyl-7-oxabicyclo[4.1.0]heptane. $^1$H NMR (CDCl$_3$, 500 MHz) δ (ppm) 3.12 (m, 4H, O—CH-epoxy ring), 2.18-0.77 (m, 18H, —CH$_2$-cyclohexane ring), 0.48 (m, 4H, —CH$_2$—Si), 0.04 (s, 24H, CH$_3$—Si).

Example 3

Synthesis of Epoxy-Silicone Oligomers

The following procedure employed for the synthesis of the epoxy-functional oligomer XIIc is typical for the synthesis of all the oligomers prepared during the course of this investigation.

First Step: Hydrosilation

Into a 100 mL round-bottom flask fitted with a magnetic stirrer and a reflux condenser were placed 8.22 g (0.025 mol) of tetrakis(dimethylsiloxy)silane, 6.21 g (0.050 mol) of 3-vinyl-7-oxabicyclo[4.1.0]heptane, 10 mL of freshly distilled toluene (or 1,4-dioxane) and approximately 7-8 mg of polymer-bound Wilkinson's catalyst. The reaction mixture was heated at 65-70° C. for 18 h. The progress of the hydrosilation reaction was followed by $^1$H NMR in CDCl$_3$ by monitoring the disappearance of the vinyl groups of VCHO and also by following the appearance of the product. After 12 h reaction, 99% of the starting epoxide was consumed.

Second Step: Dehydrocoupling

After cooling to room temperature, there were added 5-7 drops of triethylamine to the reaction mixture as an inhibitor for the epoxide ring-opening polymerization. The reaction mixture was heated at 95-100° C. for 24 h while passing air slowly through a water trap and then through the reaction mixture. The progress of the coupling reaction was periodically monitored by following the decrease in the intensity of the Si—H band at 4.7 ppm in the $^1$H-NMR.

The catalyst was removed by flash chromatography over silica gel using cyclohexane as an eluent and the filtrate stirred over anhydrous sodium sulfate and filtered. After removing the solvent using a rotary evaporator, the product was subjected to a high vacuum for 1 day at 70° C. to remove the last traces of solvent and starting materials. There were obtained 11.8 g (81% theory) of XIIc as a viscous, colorless oil. The extent of conversion was calculated from the ratio of the integrated area of the Si—H band (4.7 ppm) to the band due to the epoxide protons (3.14 ppm). $^1$H NMR (CDCl$_3$, 500

MHz) δ (ppm) 4.72 (s, Si—H); 3.14 (m, 4H, O—CH-epoxy ring); 2.19-0.82 (m, 18H, —CH$_2$— and cyclohexane ring); 0.49 (m, 4H, —CH$_2$—Si); 0.09-0.04 (m, 24H, CH$_3$—Si).

Fourier Transform Real-Time Infrared Spectroscopy (FT-RTIR) Photopolymerization Studies The photopolymerizations of the monomers and oligomers were monitored using Fourier transform real-time infrared spectroscopy (FT-RTIR). The apparatus and techniques employed for kinetic analyses using this analytical technique is described in US 2002-0137870-A1, published on 26 Sep. 2002. All FT-RTIR experiments described in this investigation were performed at room temperature using unfiltered (broadband) UV light emitted by a Hg arc source. In a given system under study, the intensity of the UV light was adjusted so that the photopolymerization could be completed within a period of approximately 150-250 seconds. Three kinetic runs were obtained for the photopolymerization of each monomer and the results averaged to obtain the final conversion versus time curve.

The kinetic parameter, $R_p/[M_o]$, for selected kinetic runs was determined from the slopes of the initial, linear portions of the irradiation time versus conversion curves, where $R_p$ and $[M_o]$ are respectively the rate of polymerization and the initial monomer concentration and the conversions are as determined from the curves at irradiation times $t_1$ and $t_2$.

Monitoring the Photopolymerization of Epoxy Silicone Monomers and Oligomers by Optical Pyrometry The apparatus and method employed for the monitoring of the photopolymerizations carried out in this investigation by optical pyrometry were described in an earlier communication from this laboratory. Samples for analysis were prepared as follows: homogeneous solutions of the desired monomer with the designated photoinitiator were prepared (all concentrations are given in mol % with respect to the monomer unless otherwise noted). A 10 δ m corona treated oriented polypropylene film was first laid down and a thin fiber mesh (cheese cloth was most often used) to serve as a spacer was placed on top of the plastic film. The liquid sample was placed onto this assembly and an identical layer of poly (propylene) film was placed over the top. The resulting sample sandwich was mounted in a 2.0 cm×2.0 cm plastic slide holder and irradiated with UV light using a UVEX Model SCU-110 mercury lamp and directed via a 95 cm liquid light pipe onto the sample. The end of the wand was placed at a predetermined distance and directed at an incident angle of 45° onto the sample window. All optical pyrometer experiments made in this investigation were conducted at ambient temperature (25-28° C.). In every case, the samples were allowed to equilibrate and establish a flat baseline for 20 seconds prior to the start of the UV irradiation. Temperature data was collected at a rate of 1 measurement per second and directly recorded and downloaded to an IBM 350-P137 personal computer for analysis.

Thermal Stability of Photopolymerized Epoxy Siloxanes

The thermal stabilities of crosslinked network polymers derived from monomers I, V and VI were measured using a Perkin Elmer Thermal Gravimetric Analyzer equipped with a TAC 7/DX Thermal Analysis Controller and 7 Series/UNIX software. Samples of films of the above monomers containing 1.0 mol % IOC10 were irradiated with UV light from a GE H37 300 W mercury arc lamp and then resulting solid polymers heated in the apparatus and the weight loss determined in static air at a rate of 10° C./min.

Example 4

Synthesis of Epoxy Functional Oligomeric Siloxanes

The new synthetic methodology described above was also applied to the preparation of several epoxy-functional oligomeric siloxanes. For example, shown above in Scheme 5 is a method for the preparation of an epoxy functional oligomeric silicone that bears pairs of reactive epoxycyclohexyl groups disposed along the backbone of the chain on every third silicon atom. The initial hydrosilation reaction of tetrakis (dimethylsiloxy)silane with two equivalents of 3-vinyl-7-oxabicyclo[4.1.0]heptane proceeded smoothly to yield an intermediate whose $^1$H-NMR spectrum is consistent with a structure, XIIa-c, possessing two epoxycyclohexyl groups and two Si—H moieties. The intermediate was not isolated but directly subjected to a rhodium catalyzed dehydrodimerization reaction. Condensation proceeded slowly at 80-100° C. in the presence of oxygen, and oligomers with different degrees of polymerization were formed. Similarly, in Scheme 6 is depicted the synthesis of an oligomer in which cyclic siloxane units bearing pendant epoxycyclohexyl groups are situated along the backbone. Although the symmetrical disubstituted intermediate XIV is shown leading to an oligomer with structure XV, it is acknowledged that the presence of other isomeric structures is also probable. Replacement of the epoxycyclohexyl groups with other types of epoxy, oxetane or vinyl ether groups can lead to still other classes of reactive oligomers.

Example 5

Photoinitiated Cationic Polymerization

Rates of the photopolymerizations of several representative dimeric monomers were evaluated using Fourier transform real-time infrared spectroscopy (RTIR). The rates of polymerization were measured by monitoring the disappearance of an infrared band due to the epoxy or oxetane groups as a function of the irradiation time. The UV light intensity employed in a given photopolymerization study was selected to allow direct comparison of the rates of polymerization of the various monomers or oligomers.

Addition polymerizations in general and cationic polymerizations, in particular, are sensitive to trace quantities of impurities that can act as inhibitors. Reactivity of V prepared by the direct, double hydrosilation of 1,1,3,3,5,5,7,7-octamethyltetrasiloxane and 3-vinyl-7-oxabicyclo[4.1.0]heptane and by the new coupling procedure was compared by RTIR. As can be noted in this study, within the limits of experimental error, these two different routes for the synthesis of V give monomers with nearly identical reactivities in cationic photopolymerization. This also implies that samples of V derived by both methods have similar purities.

The photoinitiated cationic ring-opening polymerizations of four diepoxides II, III, V, and VI were carried out at a light intensity of 410 mJ/cm$^2$ min using (4-n-decyloxyphenyl)phenyliodonium hexafluoroantimonate (IOC10) as the photoinitiator. IOC10 was selected for use in all the photopolymerization studies because it is a lipophilic photoinitiator that has good solubility in all the monomers and oligomers examined in this investigation. At a higher light intensity (1320 mJ/cm$^2$ min) the rates of polymerization of these monomers were nearly indistinguishable. All three silicon-containing monomers are highly reactive. The rates of polymerization ($R_p/[M_o]$) determined from the linear portion of the slopes of the irradiation time versus conversion curves were respectively; I, $8.9 \times 10^{-2}$ s$^{-1}$; V, $2.8 \times 10^2$ s$^{-1}$; and VI, $1.6 \times 10^{-2}$ s$^{-1}$. The order of the rates was as expected with the highest polymerization rate for the monomer with the shortest siloxane chain spacer group and the lowest rate for the longest siloxane spacer. This is reasonable since the density of the epoxy functional groups in these three difunctional monomers decreases in the same order i.e. I>V>VI. Under identical conditions, the photoinitiated cationic polymerization of 3,4-epoxycyclohexylmethyl 3',4'-epoxycyclohexane carboxylate was considerably slower ($R_p/[M_o]=0.25\times10^{-2}$ s$^{-1}$).

Another analytical technique that has been recently developed in this laboratory for monitoring the progress of photopolymerizations is optical pyrometry. This method involves following the course of the temperature of a monomer or oligomer sample during a photopolymerization by means of its infrared emission using an optical pyrometer. The faster the rate increase in the temperature of a sample, the more reactive a monomer or oligomer. The reactivity of three difunctional epoxycyclohexane monomers with different siloxane spacer lengths was studies using the optical pyrometer instrument. In accord with the corresponding RTIR results, the monomer with the shortest spacer length and the highest density of epoxy groups displays the most rapid rate of temperature increase along with the highest ultimate temperature attained during the photopolymerization. The monomers with longer chains were progressively less reactive.

A series of RTIR conversion versus time curves was generated for the photopolymerizations of epoxy monomers V and VII and oxetane monomer X using IOC10 as the photoinitiator. Also included for comparison was 3,4-epoxycyclohexylmethyl 3',4'-epoxycyclohexanecarboxylate. This study was conducted at a considerably higher light intensity (1320 mJ/cm$^2$ min) than the previous study. Under these conditions, the polymerization of VII ($R_p/[M_o]=1.20\times10^{-2}$ s$^{-1}$) was considerably faster than 3,4-epoxycyclohexylmethyl 3',4'-epoxycyclohexanecarboxylate ($R_p/[M_o]=0.33\times10^{-2}$ s$^{-1}$), although slower than V ($R_p/[M_o]=8.6\times10^{-2}$ S$^{-1}$). Difunctional oxetane monomer X is the least reactive ($R_p/[M_O]=0.086\times10^{-2}$ s$^{-1}$) monomer in this series.

The photopolymerizations of three related open-chain epoxy monomers, VII, VIII and IX were studied using optical pyrometry. VII was the most reactive monomer in this series. This may be attributed to greater value of the epoxy/MW ratio of VII as compared to that of VIII. It is noteworthy that the bisglycidyl ether, IX, is the least reactive monomer in this series. We attribute the rather poor reactivity of this and other glycidyl ethers in photo- and thermally induced cationic polymerization to two factors. First, the ether oxygen atoms in this monomer compete with the epoxide oxygens for the protons of the photogenerated acid responsible for inducing the ring-opening polymerization. Second, the presence of the two oxygen atoms of the glycidyl ether moiety provides a means for the stabilization of the protonated species through simultaneous coordination to both oxygen atoms via the formation of a pseudo five-membered ring.

Oligomers bearing polymerizable functional groups are often employed in practical applications of photopolymerization technology. However, the bulk of these applications have involved the use of oligomers that bear functional groups polymerizable under photoinduced free radical conditions. There is a conspicuous lack of equivalent oligomers that polymerize by a photoinitiated cationic mechanism. For this reason, silicone oligomers XIIIa-c and XV are of particular interest. RTIR analysis of the photopolymerizations of these four oligomers conducted at a light intensity of 420 mJ/cm$^2$ min showed that all of the oligomers were highly reactive, but there was clearly a relationship between the degree of polymerization and the reactivity of the oligomers. As the degree of polymerization increases, the rate of the polymerization decreases. This is due to two effects. First, there is an increase in the viscosity of the oligomer, which tends to slow the polymerization. Second, the greater the molecular weight of the starting oligomer, the more functional groups it possesses.

It, therefore, requires the reaction of a few of these groups to crosslink the oligomer. During crosslinking, generally the T$_g$ of the system rises slowing the rate of polymerization. The epoxy-functional silicone oligomers prepared during the course of this work undergo facile cationic photopolymerization to give colorless, transparent, glassy films.

As mentioned previously, when I was cast onto a glass plate and photopolymerized, a highly brittle, glassy, colorless film, was obtained. Similarly, oligomers XIIIa-c and XV yielded brittle inflexible films. In contrast, photopolymerized films from V showed considerable flexibility while those derived from VI with a spacer unit containing six silicon atoms was leathery. Thermal stability of polymers derived from the photopolymerization of I, V, and VI were measured by thermogravimetric analysis in air at a rate of 10° C./minute. Despite the very different flexibilities of these three polymers, their thermal stabilities were similar. The crosslinked polymers display quite good stability out to approximately 300° C. All three polymers show a characteristic weight loss at temperatures above 300° C. that occurs in two major steps. Despite the reasonably high silicon contents, in all cases, the char yields of these polymers were small.

The invention claimed is:
1. A process for preparing a cationically photopolymerizable siloxane oligomer, said process comprising
    a. combining a platinum group catalyst, a hydrosiloxane compound selected from

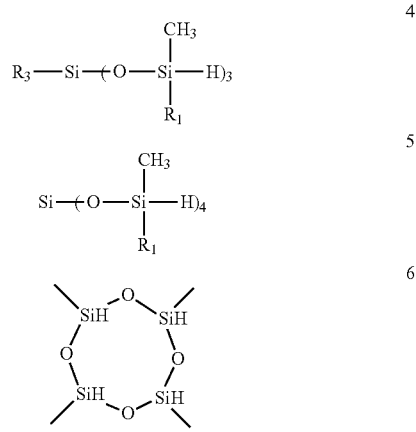

and a vinyl or allyl compound comprising cationically photopolymerizable functionality; and
    b. contacting the product with oxygen in the presence of the catalyst to form the cationically photopolymerizable multifunctional siloxane oligomer;
    wherein $R_1$ and $R_3$ are independently fluoroethyl, methyl or phenyl.
2. A process according to claim 1, wherein the vinyl or allyl compound is selected from

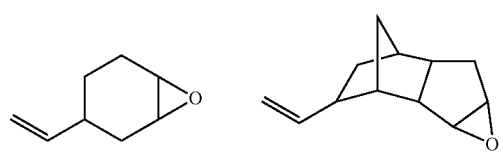

-continued

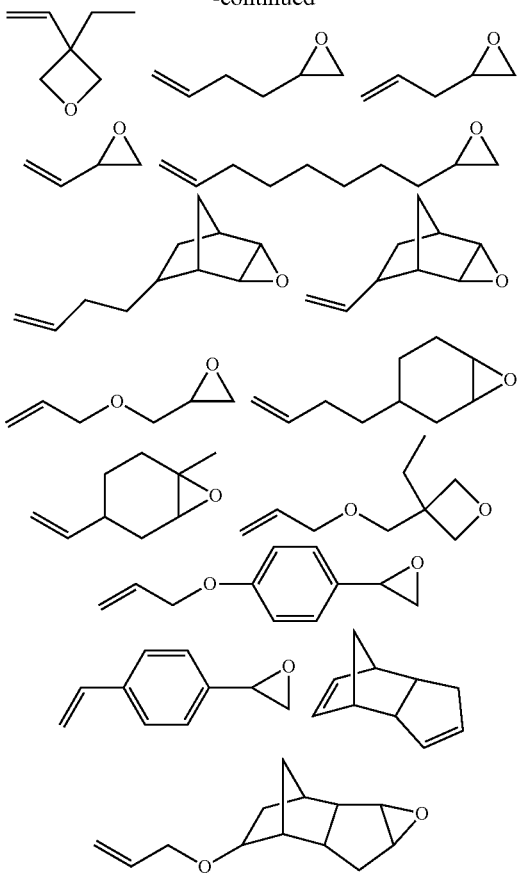

and mixtures thereof.

3. A process according to claim 1, wherein the vinyl or allyl compound is selected from the group consisting of

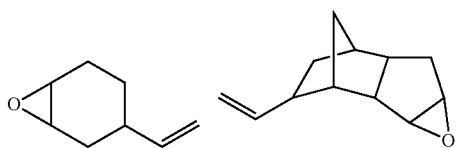

-continued

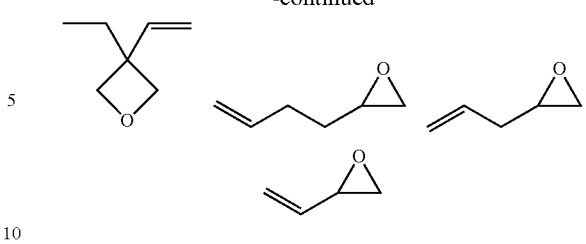

and mixtures thereof.

4. A process according to claim 1, wherein the vinyl compound is

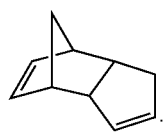

5. A process according to claim 2, additionally comprising epoxidizing the α, ω-functional siloxane to form an α, ω-epoxysiloxane.

6. A process according to claim 1, wherein the vinyl or allyl compound is

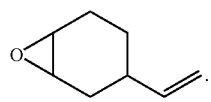

7. A process according to claim 1, wherein $R_1$ and $R_3$ are methyl.

8. A process according to claim 1, wherein the platinum group catalyst is a rhodium compound.

9. A process according to claim 1, wherein the metal catalyst is $(Ph_3P)_3RhCl$.

* * * * *